United States Patent
Herve et al.

(10) Patent No.: US 9,676,733 B2
(45) Date of Patent: Jun. 13, 2017

(54) METHOD FOR OBTAINING SOLUTIONS OF OTA IN A CONCENTRATED SULFURIC ACID MEDIUM; SAID SOLUTIONS; AND METHOD FOR PREPARING ONTA

(71) Applicants: HERAKLES, Le Haillan (FR); EURENCO, Massy (FR)

(72) Inventors: Grégoire Herve, Sarzeau (FR); Guy Jacob, Vert le Petit (FR); Guy Cagnon, Ballancourt sur Essonne (FR); Jean-Marc Bouchez, Ballancourt sur Essonne (FR)

(73) Assignees: HERAKLES, Le Haillan (FR); EURENCO, Massy (FR)

( * ) Notice: Subject to any disclaimer, the term of this patent is extended or adjusted under 35 U.S.C. 154(b) by 0 days.

(21) Appl. No.: 14/782,889

(22) PCT Filed: Apr. 4, 2014

(86) PCT No.: PCT/FR2014/050817
§ 371 (c)(1),
(2) Date: Oct. 7, 2015

(87) PCT Pub. No.: WO2014/167226
PCT Pub. Date: Oct. 16, 2014

(65) Prior Publication Data
US 2016/0046588 A1    Feb. 18, 2016

(30) Foreign Application Priority Data
Apr. 8, 2013 (FR) .................... 13 00801

(51) Int. Cl.
*C07D 249/12* (2006.01)
*C07D 249/14* (2006.01)

(52) U.S. Cl.
CPC ......... *C07D 249/12* (2013.01); *C07D 249/14* (2013.01)

(58) Field of Classification Search
CPC ....................... C07D 249/12; C07D 249/14
See application file for complete search history.

(56) References Cited

U.S. PATENT DOCUMENTS

| 4,733,610 A | 3/1988 | Lee et al. |
| 4,927,940 A | 5/1990 | Boudakian et al. |
| H861 H | 12/1990 | Collignon et al. |
| 6,583,293 B1 | 6/2003 | Kim et al. |

FOREIGN PATENT DOCUMENTS

| EP | 0 210 881 A1 | 2/1987 |
| GB | 2 218 986 A | 11/1989 |

OTHER PUBLICATIONS

International Search Report as issue in International Patent Application No. PCT/FR2014/050817, dated Jul. 23, 2014.
Chipen, G. I., "Metody Polucheniya Khimicheskikh Reaktivov I Preparatov," vol. 14, 1964, pp. 119-120, XP008166548.
Konstantinova, I.D., et al., "Chemoenzymatic Method of 1,2,4-Triazole Nucleoside Synthesis: Possibilities and Limitations," Russian Journal of Bioorganic Chemistry, 2013, vol. 39, No. 1, pp. 53-71 © Pleiades Publishing, Ltd., 2013.

*Primary Examiner* — Rebecca Anderson
*Assistant Examiner* — Karen Cheng
(74) *Attorney, Agent, or Firm* — Pillsbury Winthrop Shaw Pittman LLP

(57) ABSTRACT

A method for obtaining solutions that contain 1,2,4-triazole-5-one (OTA) in concentrated sulphuric acid, includes using 3-amino-1,2,4-triazole (ATA) as a precursor of OTA. There is also provided a method for preparing 3-nitro-1,2,4-triazole-5-one (4) (ONTA) from the solutions.

21 Claims, 2 Drawing Sheets

Figure 1:
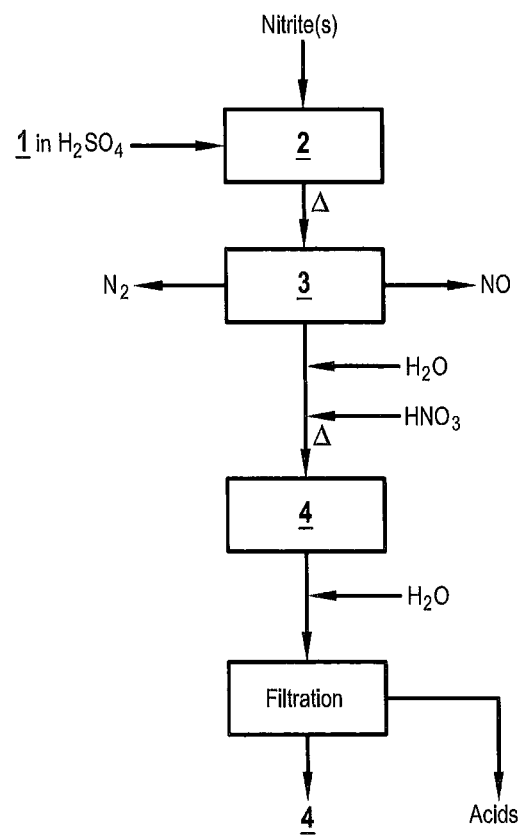

METHOD FOR OBTAINING SOLUTIONS OF OTA IN A CONCENTRATED SULFURIC ACID MEDIUM; SAID SOLUTIONS; AND METHOD FOR PREPARING ONTA

CROSS-REFERENCE TO RELATED APPLICATIONS

This application is the U.S. National Stage of PCT/FR2014/050817, filed Apr. 4, 2014, which in turn claims priority to French patent application number 1300801 filed Apr. 8, 2013.

The present invention has been designed and developed in the context of the preparation of 3-nitro-1,2,4-triazol-5-one (commonly known as oxynitrotriazole or ONTA). This compound exhibits the enormous advantage of having an explosive performance (due to its density) which is similar to that of hexogen, while exhibiting a sensitivity which is as low as that of TNT (much lower than that of said hexogen and that of octogen).

A subject matter of the present invention is more particularly:
- a novel process for the production of solutions including 1,2,4-triazol-5-one (commonly known as oxytriazole or OTA) in concentrated sulfuric acid;
- said solutions (bearing signatures of their novel process of production), and
- a process for the preparation of said 3-nitro-1,2,4-triazol-5-one (ONTA) from such solutions.

The production of these solutions from 3-amino-1,2,4-triazole (currently known as aminotriazole or ATA) and their use in the preparation of said 3-nitro-1,2,4-triazol-5-one (ONTA) (in fact, the use of said 3-amino-1,2,4-triazole (ATA) as precursor of 1,2,4-triazol-5-one (OTA) in preparing said 3-nitro-1,2,4-triazol-5-one (ONTA)) constitute the key to the present invention.

PRIOR ART

Said 3-nitro-1,2,4-triazol-5-one (ONTA) is classically obtained in 2 stages:
- a first stage of preparation of 1,2,4-triazol-5-one (OTA); and
- a second stage of nitration of said 1,2,4-triazol-5-one (OTA): OTA→ONTA.

There exist several routes of access to said 1,2,4-triazol-5-one (OTA). There exist several embodiments of its nitration.

The following have in particular been described for the preparation of 1,2,4-triazol-5-one (OTA):
- the reaction of ethyl (ethoxymethylene)carbamate with hydrazine,
- the reaction of carbohydrazide with ethyl orthoformate,
- the decarboxylation of 3-hydroxy-1,2,4-triazole-5-carboxylic acid,
- the reaction of 3-chloro-1,2,4-triazole with caustic soda, and
- the reaction of semicarbazide hydrochloride (or of semicarbazide free base) with formic acid.

The latter route of access to OTA is greatly preferred. It is developed to the industrial level.

Its use, followed by that of a nitration with nitric acid, is described in particular in the patent application EP 0 210 881 and also in the patent U.S. Pat. No. 4,733,610. According to the teaching of said application EP 0 210 881, the reaction of semicarbazide hydrochloride with formic acid is carried out in an aqueous medium, for 6 to 8 hours, at a temperature of 85-90° C. The OTA, obtained with a yield of the order of 80%, is isolated. Its nitration is subsequently carried out in 98% by weight nitric acid. According to the teaching of the patent U.S. Pat. No. 4,733,610, the OTA obtained is not isolated. It is nitrated with 70% by weight nitric acid.

The patent U.S. Pat. No. 4,927,940 also describes the preparation of OTA by reaction of semicarbazide hydrochloride with formic acid, said semicarbazide hydrochloride having been prepared in situ by reaction of hydrazine and urea.

The patent application GB 2 218 986, the document "United States Statutory Invention Registration" H 861 and the patent U.S. Pat. No. 6,583,293 themselves describe different embodiments of the nitration of OTA, in particular with concentrated nitric acid (90% by weight), in less concentrated nitric acid (70% by weight) and in sulfuric acid/nitric acid medium (98% by weight $H_2SO_4$+70% by weight $HNO_3$), respectively.

INVENTION

In such a context, the inventors have sought and optimized a process for the preparation of 3-nitro-1,2,4-triazol-5-one (ONTA) which is an alternative to the existing processes and which is particularly effective. This process, which comprises the two stages of the type indicated above: preparation of OTA and nitration of said OTA, is described below. It is particularly effective and advantageous in that:
- the products of use in its implementation (see later) are all industrial and relatively inexpensive products. This is because a person skilled in the art is not unaware that semicarbazide, in the free form or in the hydrochloride form, from which OTA is thus generally obtained (see above), is an expensive product;
- its two main stages (production of OTA (more specifically of OTA solutions (see below)) and nitration of the latter) are quantitative (the degrees of conversion ATA→OTA→ONTA can without particular difficulties be 100%). Furthermore, there are no particular difficulties in carrying them out, including at the industrial level; and
- its two main stages (see above) can be carried out successively within a single reactor. This procedure (one pot) is particularly advantageous.

According to its first subject matter, the present invention thus relates to a process for producing a solution of 1,2,4-triazol-5-one (OTA) in concentrated sulfuric acid. Such a process, which is novel, constitutes, as indicated above and specified below, the key to the present invention.

Characteristically, said process comprises:
a) the preparation, in concentrated sulfuric acid, of the diazonium hydrogensulfate of formula:

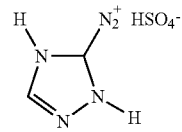

by reaction, under cold conditions, in concentrated sulfuric acid, of at least one nitrite with 3-amino-1,2,4-triazole; and
b) the heat treatment of the reaction medium including said diazonium hydrogensulfate in order to produce said solution.

Characteristically, 3-amino-1,2,4-triazole (ATA; inexpensive commercial product, used in particular as herbicide) is used as starting material (as precursor of OTA). Characteristically, it is reacted under cold conditions with (at least) one nitrite in concentrated sulfuric acid medium, i.e. it undergoes a diazotization (stage a above).

The concentrated sulfuric acid medium ($H_2SO_4/H_2O$) is suitably as concentrated as possible. The sulfuric acid employed thus generally includes at least 75% by weight, advantageously at least 80% by weight and very advantageously at least 95% by weight of sulfuric acid. Suitably, the sulfuric acid employed is 98% by weight sulfuric acid. Such a concentrated sulfuric acid is commercially available.

The concentration of ATA in said concentrated sulfuric acid is generally between 0.3 and 2 mol/l. It is advantageously between 1.3 and 1.6 mol/l. It is very advantageously between 1.4 and 1.5 mol/l. It is obviously very opportune for the ATA present to be present in the dissolved state. The concentration of ATA is furthermore suitably limited with reference to the implementation of the subsequent heat treatment. This is because, as the decomposition of the intermediate diazonium hydrogensulfate involves the release of nitrogen (i.e., the formation of foam), it is advisable to be capable of controlling this release of gas.

Said at least one participating nitrite thus participates as diazotizing agent. It can in particular be chosen from organic nitrites (such as alkyl nitrites and in particular isopentyl nitrite), alkali metal nitrites and alkaline earth metal nitrites. It advantageously consists of sodium nitrite ($NaNO_2$) and/or potassium nitrite ($KNO_2$). It very advantageously consists of sodium nitrite ($NaNO_2$). The diazotization reaction of ATA is in fact generally carried out in the presence of a single nitrite; said single nitrite thus very advantageously consists of sodium nitrite ($NaNO_2$).

The nitrite(s)/3-amino-1,2,4-triazole (ATA), generally nitrite/3-amino-1,2,4-triazole (ATA), molar ratio is generally between 1 and 2, advantageously between 1.2 and 1.4. It is in fact opportune to limit the amount of participating nitrite(s) in order to limit, on the one hand, the subsequent release (during the heat treatment) of gas (NO) subsequent to the decomposition of the excess nitrite and, on the other hand, the amount of salt present in the reaction medium, i.e. present in the OTA solution obtained, with reference to the purity of the ONTA prepared from such a solution (see below).

Said at least one nitrite is reacted with the ATA under cold conditions (with reference to the stability of the intermediate diazonium hydrogensulfate). It is generally reacted at a temperature between 0 and 10° C., advantageously between 2 and 7° C. In order to prevent any excessive heating of the reaction medium as a result of the exothermic (diazotization) reaction involved, it is highly recommended to gradually bring the reactants into contact, generally to gradually introduce the nitrite(s) into the sulfuric acid solution including the ATA. Typically, the diazotation reaction of the ATA is carried out at 5° C.

In order to produce the OTA, more specifically the solutions of OTA according to the invention (in concentrated sulfuric acid medium), the diazonium hydrogensulfate (the formula of which is shown above) obtained by diazotization of ATA (stage a explained above) is treated thermally (stage b).

This heat treatment ensures the production of OTA via the elimination of the diazo group (see the reaction scheme below). The elimination of the diazo group involves the release of nitrogen. This release is suitably controlled in order to prevent any overflowing (see above). The heat treatment also involves the decomposition of the excess nitrite, i.e. the release of NO (see above).

In order to control said heat treatment, it is thus highly recommended to carry it out according to two successive phases: a phase of slow rise in temperature with control of the release of gas (mainly nitrogen) (see above) and then a phase of maintaining at high temperature in order to produce the OTA. Said heat treatment is thus advantageously carried out according to the two phases below:

- a first phase of rise in temperature, carried out with control of the release of gas, so as to prevent any overflowing, up to a temperature T of at least 50° C., advantageously below 120° C., very advantageously up to a temperature T of 100° C., and
- a second phase of maintaining at said temperature T.

In order to ensure such a control of the release of gas, the rise in temperature of said first phase is not excessively rapid; it is advantageously carried out according to a gradient of 9° C./h to 16° C./h, very advantageously according to a gradient of 12° C./h.

Within concentrated sulfuric acid solutions, the OTA is thus obtained, according to the invention, from the ATA by a) diazotization, said diazotization resulting in the diazonium hydrogensulfate, the formula of which was given above, and then b) heat treatment; said heat treatment comprising the elimination of the diazo group from said diazonium hydrogensulfate and the conversion of the hydrogensulfate ($HSO_4^-$) group of said hydrogensulfate (see the reaction scheme below).

The production of the solutions of 1,2,4-triazol-5-one (OTA) according to the invention is thus carried out according to the reaction scheme below. Said reaction scheme is shown, in a way which is in no way limiting, with the use of sodium nitrite as diazotization nitrite.

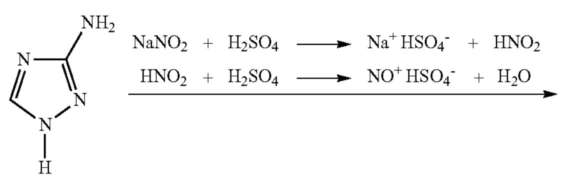

1

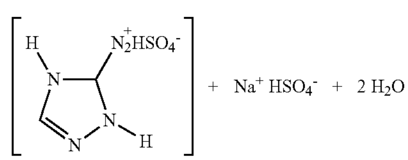

2

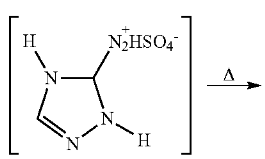

2

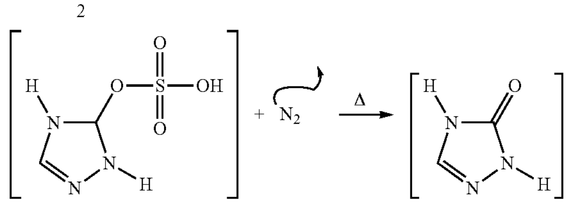

3

The production of said solutions of 1,2,4-triazol-5-one (OTA) according to the invention is very advantageously carried out in the conditions below:
a) concentrated $H_2SO_4$: 98% by weight,
ATA: 1.43 mol/l,
$NaNO_2$/ATA molar ratio: 1.27, and
reaction temperature: 5° C.;
b) heating up to 100° C., at a rate of 12° C./h, then maintenance at 100° C. for 2 hours.

According to its second subject matter, the present invention relates to the solutions of 1,2,4-triazol-5-one (OTA) in concentrated sulfuric acid obtainable by the process described above, which is a first subject matter of the present invention.

Said solutions are novel per se in that they bear novel signatures of said production process.

They include at least one salt of novel nature: hydrogensulfate(s) of the cation(s) of the nitrite(s) used as diazotizing agent (see the at least one nitrite mentioned above), sodium hydrogensulfate in a context of use of sodium nitrite. Characteristically, said solutions thus include at least one hydrogensulfate, other than the diazonium hydrogensulfate: the hydrogensulfate of the cation of the nitrite reacted with the 3-amino-1,2,4-triazole or the hydrogensulfates of the cations of the nitrites reacted with the 3-amino-1,2,4-triazole (in the event that several nitrites have been reacted).

Furthermore, they generally include ATA, more generally only traces of ATA (in the light of the quantitative conversion of said ATA into OTA according to the process of the invention).

They no longer include nitrite(s), even added in excess, insofar as the heat treatment has ensured the decomposition thereof (see the release of NO mentioned above).

Such solutions most certainly differ from similar solutions which would be obtained with OTA prepared from semicarbazide hydrochloride, with the absence of any chlorinated product within them.

According to its third subject matter, the present invention relates to a process for the preparation of 3-nitro-1,2,4-triazol-5-one (ONTA) which, in a novel fashion, uses the solutions of OTA in concentrated sulfuric acid described above (solutions which constitute the second subject matter of the present invention, a method for producing such solutions constituting the first subject matter of the present invention).

Said preparation process comprises, in a novel fashion, the nitration of such solutions (solutions of OTA in concentrated sulfuric acid medium, obtained from ATA, concentrated sulfuric acid and at least one nitrite), more specifically the nitration of the OTA present within such solutions.

The process for the preparation of ONTA according to the invention thus comprises, characteristically:
α) making available a solution of 1,2,4-triazol-5-one (OTA) in concentrated sulfuric acid according to the second subject matter of the present invention or producing a solution of 1,2,4-triazol-5-one (OTA) by the process constituting the first subject matter of the present invention (the situation is then stage α=stage a+stage b above);
then
β) nitrating said 1,2,4-triazol-5-one (OTA) by addition of concentrated nitric acid to said solution.

With reference to stage α above, it has been understood that the two alternatives are set out insofar as the solutions involved are novel per se.

Said solutions are generally obtained by carrying out said stages a and b, specified above, of the process which is the first subject matter of the present invention. Thus, in this event, the process for the preparation of ONTA according to the invention can be represented diagrammatically as follows, with the use of sodium nitrite as nitrating agent. Very optionally, the diazotization can be carried out with another nitrite (see above).

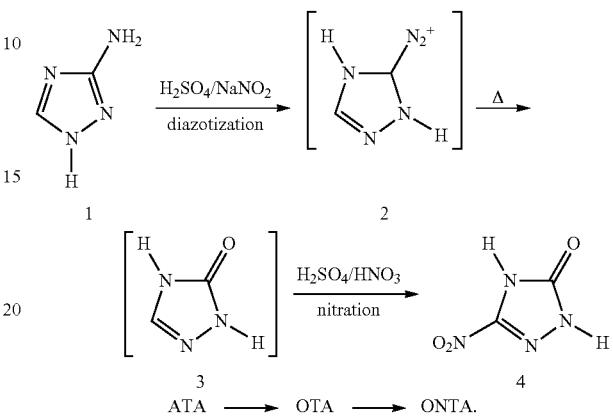

It should be noted already here that the implementation of stage α=a+b (ATA→OTA) can be completely dissociated from that of stage β (nitration: OTA→ONTA), both in terms of location and of time.

As regards the nitration (stage β), it is advantageously carried out under the conditions below:
with a nitric acid ($HNO_3/H_2O$) which is as concentrated as possible. Said concentrated nitric acid includes at least 75% by weight, advantageously at least 80% by weight and very advantageously at least 95% by weight of nitric acid. Use is advantageously made of a 98% by weight nitric acid. Such a concentrated nitric acid is commercially available;
with an $HNO_3$/1,2,4-triazol-5-one (OTA) molar ratio of between 1.9 and 2.5, advantageously between 1.95 and 2.2. The inventors have shown that there was no advantage in using large amounts of nitric acid;
at a temperature of between 50 and 70° C. At such a temperature, the nitration is generally complete in a period of 1 h 30 to 2 h 30. Below 50° C., the kinetics of the nitration reaction are too slow; above 70° C., the nitric acid decomposes: the appearance of reddish-brown vapors testifies to it. It is advantageous to carry out the nitration at a temperature of 65° C.

In order to satisfactorily carry out the nitration reaction (within a homogeneous medium, with stabilization of the temperature), it is highly recommended to add water ($H_2O$) to the solutions "to be nitrated". It is recommended to add, to said solutions, before carrying out the nitration, from 10 to 20% by weight of water, advantageously 15% by weight of water.

Starting from the solutions of OTA of the invention (solutions in concentrated sulfuric acid), the preparation of ONTA is very advantageously carried out under the conditions below:
addition (prior) of 15% by weight of water,
concentrated $HNO_3$: 98% by weight,
$HNO_3$/1,2,4-triazol-5-one (OTA) molar ratio: 1.97, and
nitration temperature: 65° C.

It was indicated above that the implementation of the nitration (stage β) can be completely dissociated from that of making available or preparing the solution to be nitrated (stage α, with generally α=a+b). It is possible, generally, to provide more or less lengthy storage of the solution obtained, before carrying out the nitration.

Furthermore, the solution to be nitrated can entirely be obtained on a different site from that of its nitration or on one and the same site but in another reactor (offsetting in space, of more or less amplitude, which a priori involves a consequent offsetting in time).

According to another alternative form, by far preferred, the process for the preparation of ONTA according to the invention comprises:
  a first stage of producing a solution of 1,2,4-triazol-5-one (OTA) in concentrated sulfuric acid according to the process described above (stage α=stage a+stage b), and
  a second stage of nitrating said 1,2,4-triazol-5-one (OTA) by addition of concentrated nitric acid to said solution (stage β);
said first and second stages being carried out within one and the same reactor.

The OTA is thus prepared in situ for its nitration. The operations of producing the OTA and of nitrating said OTA are carried out in the same reactor. The process involved is a one pot process. A person skilled in the art is not unaware of the advantages of this type of process, in particular for its implementation on the industrial scale.

According to this preferred alternative embodiment of the novel process for the preparation of ONTA of the invention, the reactions explained above: ATA→OTA→ONTA, are thus successively carried out (with or without offsetting in time, generally without offsetting in time) within one and the same reactor.

Whatever is finally the exact alternative embodiment of the process of the preparation of ONTA according to the invention (exact procedure; stages α and β carried out or not carried out on one and the same site, in or not in one and the same reactor, with or without offsetting in time), it is generally opportune to recover said ONTA thus obtained in concentrated sulfuric medium.

For such a recovery, a precipitation (crystallization), subsequent to a lowering of the temperature of the reaction medium, followed by filtration, is recommended. Said filtration is itself advantageously followed by pulling dry the crystals recovered.

In order to obtain a product (precipitated, crystallized) which is as pure as possible, a precipitation which is selective with regard to the salts present (mainly of the hydrogensulfate(s) present) is targeted. In order to carry out such a selective precipitation, it is recommended to add water to the cooled reaction medium (including said ONTA) (during cooling and/or on conclusion of the cooling, generally on conclusion of said cooling), said water contributing to the maintenance in solution of the salts present (of the hydrogensulfate(s) present). The addition of 8 to 15% by weight, preferably of 10% by weight, of water is highly recommended.

The cooling of the reaction medium is furthermore advantageously carried out to (only) a temperature between 8 and 12° C., advantageously to 10° C. The inventors have shown that cooling to lower temperatures results in the precipitation of an ONTA of lower purity.

The selectivity of the precipitation can in fact be optimized as a result of the presence of water, in a sufficient amount (see above) and if the cooling is carried out to (only) a temperature between 8 and 12° C., advantageously to 10° C.

A person skilled in the art has already noted all the interest of the invention and all its advantages. As indicated in the introduction of the present text, the present invention makes it possible to obtain ONTA without resorting to expensive products (only to ATA, to at least one nitrite and to concentrated $H_2SO_4$ and $HNO_3$ solutions), via two quantitative stages (production of the OTA, nitration of the OTA) (degrees of conversion at 100% can be obtained without particular difficulties) which, suitably, can be carried out in a single reactor.

Furthermore, the process of the invention, with in particular the addition of water in the phase of recovery of the ONTA (in order to maintain in solution the salt(s) formed because the involvement of at least one nitrite (diazotizing agent for the ATA) upstream), makes it possible to obtain ONTA of very high purity (98% by weight, generally after pulling dry (i.e., freed from the aqueous mother liquors)). With reference to the purity of the ONTA finally recovered, the following may be added. If the maximum ONTA is precipitated (for the purpose of "optimizing" the final yield of the reaction), the impurities present in the medium (hydrogensulfate salt(s)) are unfortunately jointly precipitated, at least in part. If the ONTA is selectively precipitated (thus with an "optimum" degree of purity), this is to the detriment of the yield. An advantageous compromise can be found. The degree of purity (98% by weight) indicated above was obtained with a yield of 55% (final dry ONTA/starting ATA).

EXAMPLE AND FIGURES

The intention is now to illustrate, in a way which is in no way limiting, the various aspects of the invention by the example below and the appended figures.

FIG. 1 is a flow sheet of an alternative embodiment (one pot) of the process for the preparation of ONTA according to the invention, an alternative form without intermediate storage of the solution of OTA, which is obtained in a first step, in concentrated sulfuric acid.

Figure 2:
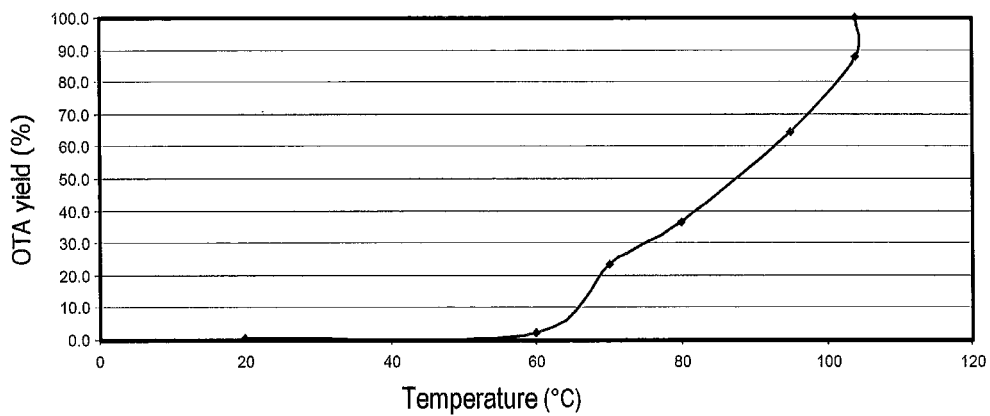
Figure 3:
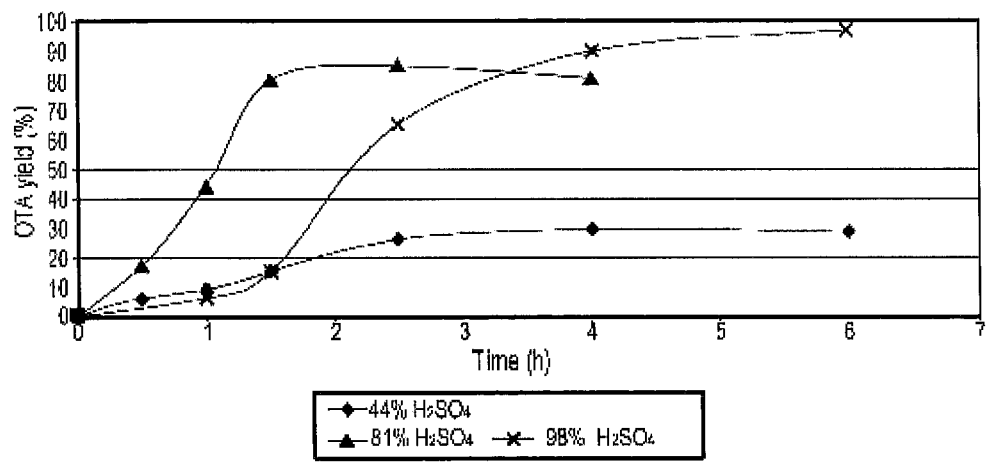
Figure 4:
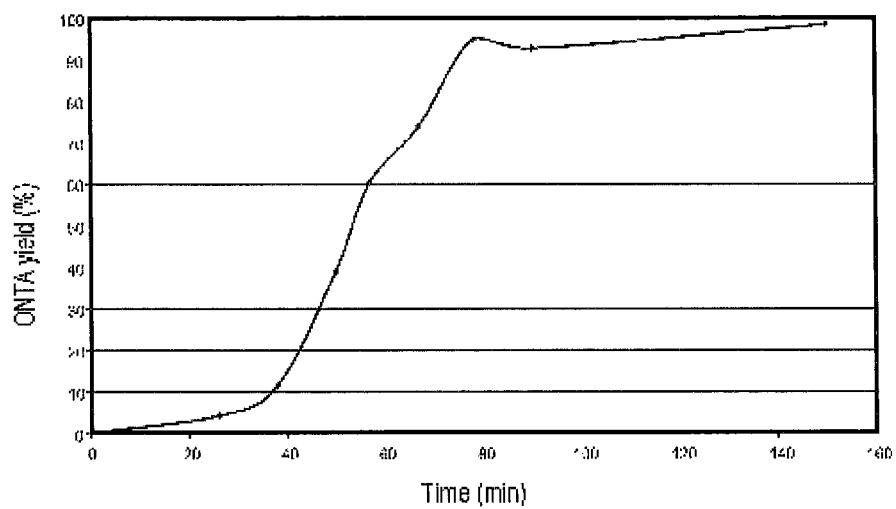

FIGS. 2 to 4 are curves respectively representing:
  for FIG. 2, the increase in the OTA yield during the rise in temperature of the reactor (stage b (heat treatment) of the example below);
  for FIG. 3, the increase in the OTA yield under the same conditions of rise in temperature but within more or less concentrated sulfuric acid solutions (44%, 81% and 98% by weight),
  for FIG. 4, the increase in the ONTA yield as a function of the time, after running in the nitric acid (thus during the implementation of the nitration: stage β of the example below).

Further information considering these curves is given in the example below.

As regards FIG. 1, there has been indicated, as has already been done in the reaction schemes given upstream in the description:
as 1,3-amino-1,2,4-triazole=ATA,
as 2, the diazonium hydrogensulfate (="diazotized ATA"),
as 3, 1,2,4-triazol-5-one=OTA, and
as 4, 3-nitro-1,2,4-triazol-5-one=ONTA.

It is understood that the at least one nitrite is reacted with 1 in sulfuric acid in order to diazotize it.

The heat treatment (Δ) ensures the elimination of the diazo group (hence the release of $N_2$), it somewhat decomposes the unreacted nitrite (hence the release of NO) and makes it possible to obtain 3.

This first part of the flow sheet corresponds to the process of producing a solution of 3 in concentrated sulfuric acid (first subject matter of the present invention).

The second part of the flow sheet corresponds to the preparation and to the recovery of 4 (third subject matter of the present invention).

The nitration (with heating: Δ) is carried out under "optimal" conditions as a result of the addition of H₂O before the addition of the nitric acid.

For the recovery (by precipitation) of 4, "minimally contaminated" by hydrogensulfate or hydrogenosulfates present, cooling is carried out to a temperature between 8 and 12° C. and water is again added.

The precipitated (crystallized) ONTA is recovered by filtration. The old acids (H₂SO₄+HNO₃) are recovered and can be separated. The nitric acid is advantageously recycled.

The process exemplified, as represented diagrammatically in FIG. 1, is a one pot process.

EXAMPLE

A. Synthesis of OTA: Production of a Solution of OTA in Concentrated Sulfuric Acid 144 g (1.714 mol) of 3-amino-1,2,4-triazole (commercial ATA) are added to 1.2 l of concentrated sulfuric acid (98% by weight commercial concentrated sulfuric acid) cooled before to 5° C.

The mixture is cooled to 5° C.

150 g (2.174 mol) of sodium nitrite (NaNO₂) are gradually added at this temperature of 5° C. Care is taken not to exceed 10° C.

At the end of the introduction of the sodium nitrite, the reaction medium is gradually heated to 100° C. under a temperature gradient of 12° C./h. Once this temperature of 100° C. is reached (after approximately 8 hours), the reaction medium is left stirring for 2 hours (at said temperature of 100° C.).

The progression of the reaction is monitored by high performance liquid chromatography (HPLC) after external calibration (using a commercial OTA). The OTA yield is measured on samples withdrawn at different temperatures (diluted in water in order to halt the reaction).

FIG. 2 (it is seen that a yield of 100% can be achieved) and the 98% by weight H₂SO₄ curve of FIG. 3 were thus drawn up.

This same synthesis and these same measurements were carried out under the same conditions with less concentrated sulfuric acids (see the other two curves of FIG. 3: 44% by weight H₂SO₄ and 81% by weight H₂SO₄).

FIG. 3 clearly shows the advantage of carrying out the reaction with sulfuric acid which is as concentrated as possible.

The solution obtained can be used directly for the preparation of ONTA.

It can also be stored and/or transported in order to act as starting material in a subsequent synthesis of ONTA.

In the context of the alternative embodiment exemplified, it was used, at once, for the synthesis (one pot) of ONTA.

B. Synthesis and Recovery of ONTA 509 g (28.28 mol) of water are added with stirring to the solution of OTA obtained (in 98% sulfuric acid), followed by 213 g (3.38 mol) of concentrated nitric acid (98% by weight commercial nitric acid).

After introduction of the nitric acid, the medium is brought to 65° C. and left stirring at this temperature for 2 hours.

Samples are withdrawn in order to monitor the progression of the nitration (once the temperature of the reaction medium has reached 65° C.). Said samples are analyzed after external calibration (using a commercial ONTA). The results are shown in FIG. 4. It is seen that a very high yield can be obtained.

The following procedure was carried out for the recovery of the ONTA prepared.

The reaction medium is cooled to 10° C. (at expiration of the 2 hours). An amount of 293 g (16.28 mol) of water is then added while maintaining the temperature at 10° C. The crystallized ONTA is then filtered off and then pulled dry on a Büchner filter.

The weight of wet ONTA recovered is 403 g.

The HPLC analysis (of the ONTA recovered) makes it possible to establish, after external calibration (with commercial ONTA), a yield of 96% of wet product (/to the starting ATA).

The nature of the product obtained (ONTA) was also confirmed by ¹³C NMR.

¹³C NMR (DMSO, 100 MHz): δ 158.22 ppm (s), 139.24 ppm (s).

The invention claimed is:

1. A process for the preparation of 3-nitro-1,2,4-triazol-5-one, the process comprising:
producing a solution of 1,2,4-triazol-5-one in concentrated sulfuric acid, said producing comprising
preparing, in concentrated sulfuric acid, diazonium hydrogensulfate of formula:

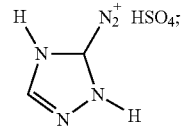

by reaction, under cold conditions, in concentrated sulfuric acid, of at least one nitrite with 3-amino-1,2,4-triazole;
heating the reaction medium including said diazonium hydrogensulfate in order to produce said solution of 1,2,4-triazol-5-one; and
nitrating said 1,2,4-triazol-5-one by addition of concentrated nitric acid to said solution.

2. The process as claimed in claim 1, wherein said concentrated sulfuric acid includes at least 75% by weight of sulfuric acid.

3. The process as claimed in claim 1 wherein the concentration of said 3-amino-1,2,4-triazole in the concentrated sulfuric acid is between 0.3 and 2 mol/l.

4. The process as claimed in claim 1, wherein said at least one nitrite is chosen from organic nitrites, alkali metal nitrites and alkaline earth metal nitrites.

5. The process as claimed in claim 1, wherein the nitrite(s)/3-amino-1,2,4-triazole molar ratio is between 1 and 2.

6. The process as claimed in claim 1, wherein said at least one nitrite is reacted with said 3-amino-1,2,4-triazole at a temperature between 0° C. and 10° C.

7. The process as claimed in claim 1, wherein said heating comprises two phases:
a first phase of rise in temperature, carried out with control of the release of gas, so as to prevent any overflowing, up to a temperature T of at least 50° C., and
a second phase of maintaining at said temperature T.

8. The process as claimed in claim 7, wherein the rise in temperature of the first phase is carried out according to a gradient of 9° C./h to 16° C./h.

9. The process as claimed in claim 1, wherein said concentrated nitric acid includes at least 75% by weight of nitric acid.

10. The process as claimed in claim 1, wherein said concentrated nitric acid is added in an $HNO_3$/1,2,4-triazol-5-one molar ratio of between 1.9 and 2.5.

11. The process as claimed in claim 1, wherein from 10 to 20% by weight of water ($H_2O$) is added to said solution, before said addition of concentrated nitric acid.

12. The process as claimed in claim 1, wherein the producing and nitrating occur in a same reactor.

13. The process as claimed in claim 1, further comprising recovering the 3-nitro-1,2,4-triazol-5-one, said recovering comprising a precipitation of the latter by cooling the reaction medium obtained on conclusion of the nitration.

14. The process as claimed in claim 13, wherein the cooling is carried out to a temperature of between 8 and 12° C.

15. The process as claimed in claim 1, wherein said concentrated sulfuric acid includes at least 95% by weight of sulfuric acid.

16. The process as claimed in claim 1, wherein the concentration of said 3-amino-1,2,4-triazole in the concentrated sulfuric acid is between 1.3 and 1.6 mol/l.

17. The process as claimed in claim 1, wherein said at least one nitrite consists of sodium nitrite ($NaNO_2$).

18. The process as claimed in claim 7, wherein the temperature T is below 120° C.

19. The process as claimed in claim 1, wherein said concentrated nitric acid includes at least 95% by weight of nitric acid.

20. The process as claimed in claim 10, wherein said concentrated nitric acid is added in an $HNO_3$/1,2,4-triazol-5-one molar ratio of between 1.95 and 2.2.

21. The process as claimed in claim 13, wherein from 8 to 15% by weight of water ($H_2O$) are added to said cooled reaction medium for selective precipitation of said 3-nitro-1,2,4-triazol-5-one.

* * * * *